United States Patent
Fry

(10) Patent No.: US 11,313,771 B1
(45) Date of Patent: Apr. 26, 2022

(54) SAMPLE COLLECTION APPARATUS FOR SCENT DETECTION

(71) Applicant: The Government of the United States of America, as represented by the Secretary of Homeland Security, Washington, DC (US)

(72) Inventor: Mark Fry, Marco Island, FL (US)

(73) Assignee: The Government of the United States of America, as renresenten by the Secretary of Homeland Securitv, Washington, DC (US)

( * ) Notice: Subject to any disclaimer, the term of this patent is extended or adjusted under 35 U.S.C. 154(b) by 0 days.

(21) Appl. No.: 17/210,326

(22) Filed: Mar. 23, 2021

Related U.S. Application Data

(60) Provisional application No. 63/092,903, filed on Oct. 16, 2020.

(51) Int. Cl.
  *G01N 1/22* (2006.01)
  *G01N 1/28* (2006.01)
  *G01N 1/02* (2006.01)

(52) U.S. Cl.
  CPC ......... *G01N 1/2211* (2013.01); *G01N 1/2247* (2013.01); *G01N 1/28* (2013.01);
  (Continued)

(58) Field of Classification Search
  CPC .. G01N 2001/022; G01N 1/2202; G01N 1/24; G01N 2001/2223; G01N 2001/025; G01N 1/22; G01N 2001/024
  See application file for complete search history.

(56) References Cited

U.S. PATENT DOCUMENTS

| | | | | | |
|---|---|---|---|---|---|
| 3,998,101 | A | * | 12/1976 | Bradshaw | G01N 1/2273 |
| | | | | | 73/864 |
| 4,012,690 | A | * | 3/1977 | Heytow | G01V 3/105 |
| | | | | | 324/243 |

(Continued)

FOREIGN PATENT DOCUMENTS

| CN | 203175215 U | * | 9/2013 |
|---|---|---|---|
| FR | 3024991 A1 | * | 2/2016 |

(Continued)

OTHER PUBLICATIONS

ESPACENET Machine Translation of JP-H-02243934 A Which Originally Published on Sep. 28, 1990. (Year: 1990).*

(Continued)

*Primary Examiner* — David A. Rogers
(74) *Attorney, Agent, or Firm* — Lavanya Ratnam; Kelly G. Hyndman; Robert W. Busby

(57) ABSTRACT

In an example, a sample collection apparatus to collect sample from a detection subject includes a circumferential ring tubing surrounding an interior and configured to be moved between bottom ring tubing position and top ring tubing position. The circumferential ring tubing includes air nozzles along a circumferential length of the ring tubing to direct air flow toward the interior as the ring tubing is moved from the top ring tubing position to the bottom ring tubing position, to blow air toward the detection subject in a sample collection zone in the interior and to push a sample of the detection subject via an air flow toward a platform on which the detection subject is positioned. The sample includes particles and/or vapor of the detection subject. A receptacle is disposed below the platform to collect the sample carried by the air flow through collection openings of the platform to the receptacle.

20 Claims, 7 Drawing Sheets

(52) U.S. Cl.
CPC .................. *G01N 2001/024* (2013.01); *G01N 2001/2223* (2013.01)

(56) References Cited

U.S. PATENT DOCUMENTS

| | | | | |
|---|---|---|---|---|
| 4,045,997 A * | 9/1977 | Showalter | ........... | G01N 33/0011 73/23.2 |
| 4,896,547 A * | 1/1990 | Arney | ................... | G01N 1/2273 73/863.81 |
| 4,909,089 A * | 3/1990 | Achter | ..................... | G01N 1/24 73/863.11 |
| 4,964,309 A * | 10/1990 | Jenkins | ..................... | E06B 5/00 340/632 |
| 5,753,832 A * | 5/1998 | Bromberg | ............ | G01N 1/2205 73/864.24 |
| 5,915,268 A * | 6/1999 | Linker | ................... | G01V 9/007 73/23.2 |
| 6,073,499 A * | 6/2000 | Settles | ................. | G01N 1/2214 73/864.34 |
| 6,334,365 B1* | 1/2002 | Linker | ................. | G01N 1/2214 73/864.71 |
| 6,375,697 B2* | 4/2002 | Davies | ................. | B08B 5/02 454/187 |
| 6,610,977 B2* | 8/2003 | Megerle | ................. | G01N 1/2202 250/286 |
| 6,651,520 B1* | 11/2003 | Allen | ................... | G01N 1/2214 137/512.15 |
| 6,708,572 B2* | 3/2004 | Jenkins | ................ | G01N 1/2202 73/28.04 |
| 6,790,249 B2* | 9/2004 | Davies | ..................... | B08B 5/02 454/187 |
| 6,797,944 B2* | 9/2004 | Nguyen | ................... | G01N 1/24 250/286 |
| 6,806,450 B2* | 10/2004 | Nakashige | ............ | G01N 27/68 250/282 |
| 6,840,122 B1* | 1/2005 | Jenkins | ................ | G01N 1/2202 73/864.33 |
| 6,946,300 B2* | 9/2005 | Nguyen | ................... | G01N 1/24 356/36 |
| 6,984,524 B2* | 1/2006 | Nguyen | ................... | G01N 21/76 250/361 C |
| 7,141,786 B2* | 11/2006 | McGann | ............ | G01N 15/0618 250/287 |
| 7,225,694 B2* | 6/2007 | Said | ........................ | F16H 25/20 74/89.35 |
| 7,299,679 B2* | 11/2007 | Lovell | ................... | G01N 1/2202 73/31.05 |
| 7,316,152 B2* | 1/2008 | Strohmeyer | .............. | B07C 1/00 209/606 |
| 7,328,603 B1* | 2/2008 | Strohmeyer | .............. | B07C 1/00 209/606 |
| 7,357,043 B2* | 4/2008 | Cumming | ................ | G01N 1/24 73/864.33 |
| 7,365,536 B2* | 4/2008 | Crowley | .............. | G01R 33/441 324/300 |
| 7,458,248 B2* | 12/2008 | Carlson | ..................... | B07C 1/00 340/632 |
| 7,503,204 B2* | 3/2009 | Strohmeyer | .............. | B07C 1/00 209/606 |
| 7,543,478 B2* | 6/2009 | Burroughs | ............ | G01N 1/2202 73/28.01 |
| 7,594,422 B2* | 9/2009 | Perry | .................. | G01N 1/2214 73/1.02 |
| 7,721,588 B2* | 5/2010 | Perry | ................ | B01D 46/0001 73/28.01 |
| 7,750,631 B2* | 7/2010 | Crowley | ................ | G01V 3/104 324/307 |
| 7,905,154 B2* | 3/2011 | Jones, Jr. | ................ | G01N 1/06 73/864.81 |
| 7,913,540 B2* | 3/2011 | Brasfield | ............ | G01N 33/0001 73/23.34 |
| 7,942,033 B2* | 5/2011 | Jenkins | ................ | G01N 27/622 73/31.01 |
| 7,997,119 B2* | 8/2011 | Wu | ......................... | G01N 1/14 73/31.03 |
| 8,033,158 B2* | 10/2011 | Strohmeyer | ......... | G01N 1/2226 73/28.01 |
| 8,129,691 B2* | 3/2012 | Hu | ........................... | G01N 1/02 250/390.01 |
| 8,149,115 B2* | 4/2012 | Arcaini | ................. | G01N 1/2273 340/540 |
| 8,222,042 B2* | 7/2012 | Dugan | ..................... | G01N 1/02 436/148 |
| 8,272,280 B2* | 9/2012 | Jones, Jr. | ................ | G01N 33/12 73/864.81 |
| 8,307,723 B2* | 11/2012 | Novosselov | ......... | G01N 1/2202 73/864.32 |
| 8,424,365 B2* | 4/2013 | Crowley | ................ | G01N 24/084 73/31.01 |
| 8,429,987 B1* | 4/2013 | Linker | ...................... | G01N 1/22 73/864.33 |
| 8,646,340 B2* | 2/2014 | Zhang | ...................... | G01N 1/22 73/863.11 |
| 8,756,975 B2* | 6/2014 | Wu | ......................... | G01N 1/405 73/31.05 |
| 8,806,914 B2* | 8/2014 | Brasfield | ............ | G01N 33/0001 73/23.34 |
| 9,048,076 B2* | 6/2015 | Stott | ......................... | G01N 1/22 |
| 9,075,028 B2* | 7/2015 | Pruett | ................ | G01N 33/0004 |
| 9,134,205 B2* | 9/2015 | Hillis | ................... | G01N 1/2202 |
| 9,261,437 B2* | 2/2016 | Kashima | ............... | G01N 1/2211 |
| 9,303,446 B2* | 4/2016 | Fougeroux | ............... | G01N 1/24 |
| 9,335,236 B2* | 5/2016 | Bry | ......................... | G01N 1/24 |
| 9,568,028 B2* | 2/2017 | Nowak | ..................... | F15B 15/20 |
| 9,696,288 B2* | 7/2017 | Kashima | ................ | G01N 1/2202 |
| 9,835,602 B2* | 12/2017 | Brasfield | ................ | G07C 9/30 |
| 10,123,509 B2 | 11/2018 | Pearce et al. | | |
| 10,175,198 B2* | 1/2019 | Briglin | ................. | G01N 27/64 |
| 10,274,404 B1* | 4/2019 | Novosselov | ............ | B05B 1/005 |
| 10,274,469 B2* | 4/2019 | Brasfield | ................ | G07C 9/30 |
| 10,914,714 B2* | 2/2021 | Salinas | ................ | G01N 30/7206 |
| 2001/0049926 A1* | 12/2001 | Davies | ................. | G01N 1/2214 55/385.2 |
| 2003/0085348 A1* | 5/2003 | Megerle | ................ | G01N 1/2202 250/287 |
| 2006/0081073 A1* | 4/2006 | Vandrish | ................ | G01N 1/2202 73/864.33 |
| 2007/0056392 A1* | 3/2007 | Cumming | ................ | G01N 1/24 73/864.33 |
| 2009/0077908 A1* | 3/2009 | Brasfield | ............... | F41H 11/132 52/198 |
| 2009/0162196 A1* | 6/2009 | Drolet | .................... | F04D 25/084 415/224 |
| 2010/0245081 A1* | 9/2010 | Arcaini | ................. | G01N 30/00 340/540 |
| 2011/0203349 A1* | 8/2011 | Reese | ..................... | A01K 15/02 73/23.34 |
| 2012/0047996 A1* | 3/2012 | Reese | ................ | G01N 33/0001 73/31.05 |
| 2012/0103060 A1* | 5/2012 | Brasfield | .................. | G07C 9/10 73/23.34 |
| 2012/0137802 A1* | 6/2012 | Balducci | .............. | F16H 25/2021 74/89.23 |
| 2014/0209192 A1* | 7/2014 | Lawrence | ................. | G01N 1/02 137/565.01 |
| 2014/0311219 A1* | 10/2014 | Brasfield | ............ | G01N 33/0057 73/23.34 |
| 2015/0311053 A1* | 10/2015 | Stott | ........................ | H01J 49/00 250/288 |
| 2018/0045696 A1* | 2/2018 | Brasfield | ............ | G01N 33/0057 |
| 2019/0302045 A1* | 10/2019 | Uematsu | .................. | G01M 3/02 |

FOREIGN PATENT DOCUMENTS

| | | | | |
|---|---|---|---|---|
| JP | | 02243934 A | * 9/1990 | |
| WO | WO-2004108580 A1 | * 12/2004 | ......... | E05F 15/632 |
| WO | WO-2012024619 A3 | * 7/2012 | ......... | G01N 33/0057 |

(56) References Cited

OTHER PUBLICATIONS

ESPACENET Machine Translation of CN 203175215 U Which Originally Published on Sep. 4, 2013. (Year: 2013).*

* cited by examiner

SAMPLE COLLECTION APPARATUS FOR SCENT DETECTION

CROSS-REFERENCE TO RELATED APPLICATIONS

The application claims the benefit of priority from U.S. Provisional Patent Application No. 63/092,903, filed on Oct. 16, 2020, entitled CANINE TESTING AND DETECTION AIDE, the disclosure of which is incorporated by reference in its entirety.

SUMMARY STATEMENT OF GOVERNMENT INTEREST

The present invention was made by employees of the United States Department of Homeland Security in the performance of their official duties. The U.S. Government has certain rights in this invention.

FIELD

The discussion below relates generally to systems and methods of facilitating detection and testing of illicit substances utilizing canine or the like.

BACKGROUND

U.S. Pat. No. 10,123,509 discloses enhancing air flow with fans in vapor wake detection for detecting explosives and other illicit substances. With vapor wake detection, a handler positions a canine in a desired location and the canine detects scents in the air that come to the canine. When the canine detects a trained scent such as a bomb scent, the canine follows behind the carrier of the item with the scent and leads the handler to the carrier.

SUMMARY

Embodiments of the present invention are directed to apparatuses and methods for directing not only vapor but also particles from a detection subject or carrier to a detection area for detecting explosives or other illicit substances, for instance, by a canine trained in scent detection. In some embodiments, a canine testing and detection aide is more focused and separates the dog from the detection subjects. The sample collection apparatus may be configured to collect particles as well as vapor of the detection subject for detection and thus greatly increases the sample size.

In accordance with an aspect, a sample collection apparatus to collect sample from a detection subject comprises: a circumferential ring tubing surrounding an interior and configured to be moved generally vertically between a bottom ring tubing position and a top ring tubing position, the circumferential ring tubing including a plurality of air nozzles along a circumferential length of the circumferential ring tubing to direct air flow toward the interior as the circumferential ring tubing is moved from the top ring tubing position to the bottom ring tubing position, to blow air toward the detection subject in a sample collection zone in the interior of the circumferential ring tubing as the circumferential ring tubing is moved from the top ring tubing position to the bottom ring tubing position, and to push a sample of the detection subject via an air flow forward toward a platform on which the detection subject is positioned, the sample including at least one of particles and vapor of the detection subject; and a receptacle disposed below the platform to collect the sample of the detection subject carried by the air flow through a plurality of collection openings of the platform to the receptacle.

Another aspect is directed to a sample collection method to collect sample from a detection subject. The method comprises: placing a circumferential ring tubing at a ring tubing initiation position at or near an initiation end of the detection subject, the circumferential ring tubing surrounding an interior; moving the circumferential ring tubing translationally from the ring tubing initiation position to a ring tubing collection position at or near a platform to which the detection subject is connected, blowing air through a plurality of air nozzles along a circumferential length of the circumferential ring tubing to direct air flow toward the interior as the circumferential ring tubing is moved from the ring tubing initiation position to the ring tubing collection position to blow air toward the detection subject in a sample collection zone in the interior of the circumferential ring tubing as the circumferential ring tubing is moved from the ring tubing initiation position to the ring tubing collection position, and to push a sample of the detection subject via an air flow forward toward the platform to which the detection subject is connected, the sample including at least one of particles and vapor of the detection subject; and collecting the sample of the detection subject carried by the air flow in a receptacle disposed adjacent the platform through a plurality of collection openings of the platform to the receptacle.

In accordance with another aspect, a sample collection apparatus to collect sample from a detection subject comprises: a sample receptacle; and a circumferential ring tubing surrounding an interior and configured to be moved between an ring tubing initiation position and a ring tubing collection position, the circumferential ring tubing including a plurality of air nozzles along a circumferential length of the circumferential ring tubing to direct air flow toward the interior as the circumferential ring tubing is moved from the ring tubing initiation position forward to the ring tubing collection position, to blow air toward the detection subject in a sample collection zone in the interior of the circumferential ring tubing as the circumferential ring tubing is moved from the ring tubing initiation position to the ring tubing collection position, and to push a sample of the detection subject via an air flow forward toward the sample receptacle, the sample including at least one of particles and vapor of the detection subject.

Other features and aspects of various examples and embodiments will become apparent to those of ordinary skill in the art from the following detailed description which discloses, in conjunction with the accompanying drawings, examples that explain features in accordance with embodiments. This summary is not intended to identify key or essential features, nor is it intended to limit the scope of the invention, which is defined solely by the claims.

BRIEF DESCRIPTION OF THE DRAWINGS

The attached drawings help explain the embodiments described below.

DETAILED DESCRIPTION

A number of examples or embodiments of the present invention are described, and it should be appreciated that the present invention provides many applicable inventive concepts that can be embodied in a variety of ways. The embodiments discussed herein are merely illustrative of ways to make and use the invention and are not intended to limit the scope of the invention. Rather, as will be appreciated by one of skill in the art, the teachings and disclosures herein can be combined or rearranged with other portions of this disclosure along with the knowledge of one of ordinary skill in the art.

Figure 1B:
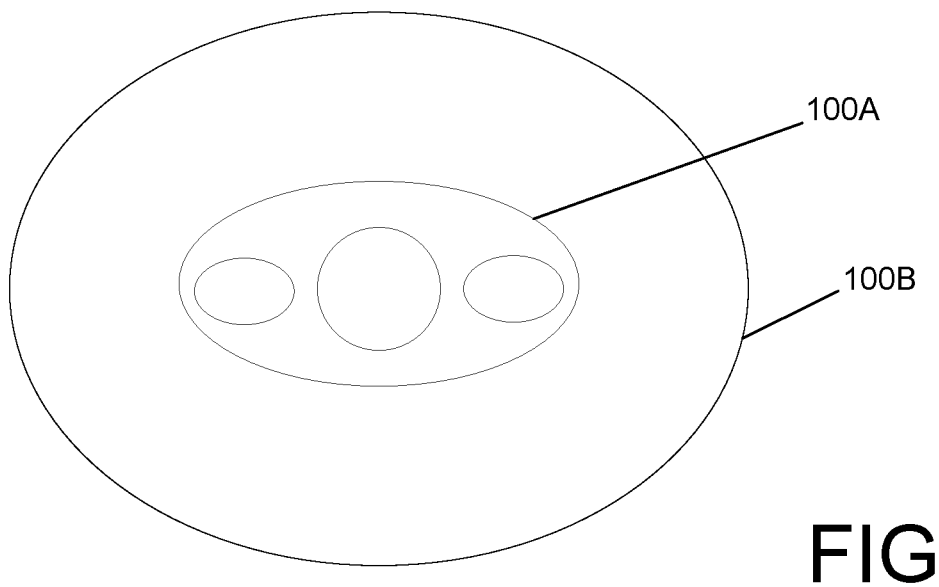
FIG. 1B is a simplified top view of the apparatus of FIG. 1A.
Figure 1A:
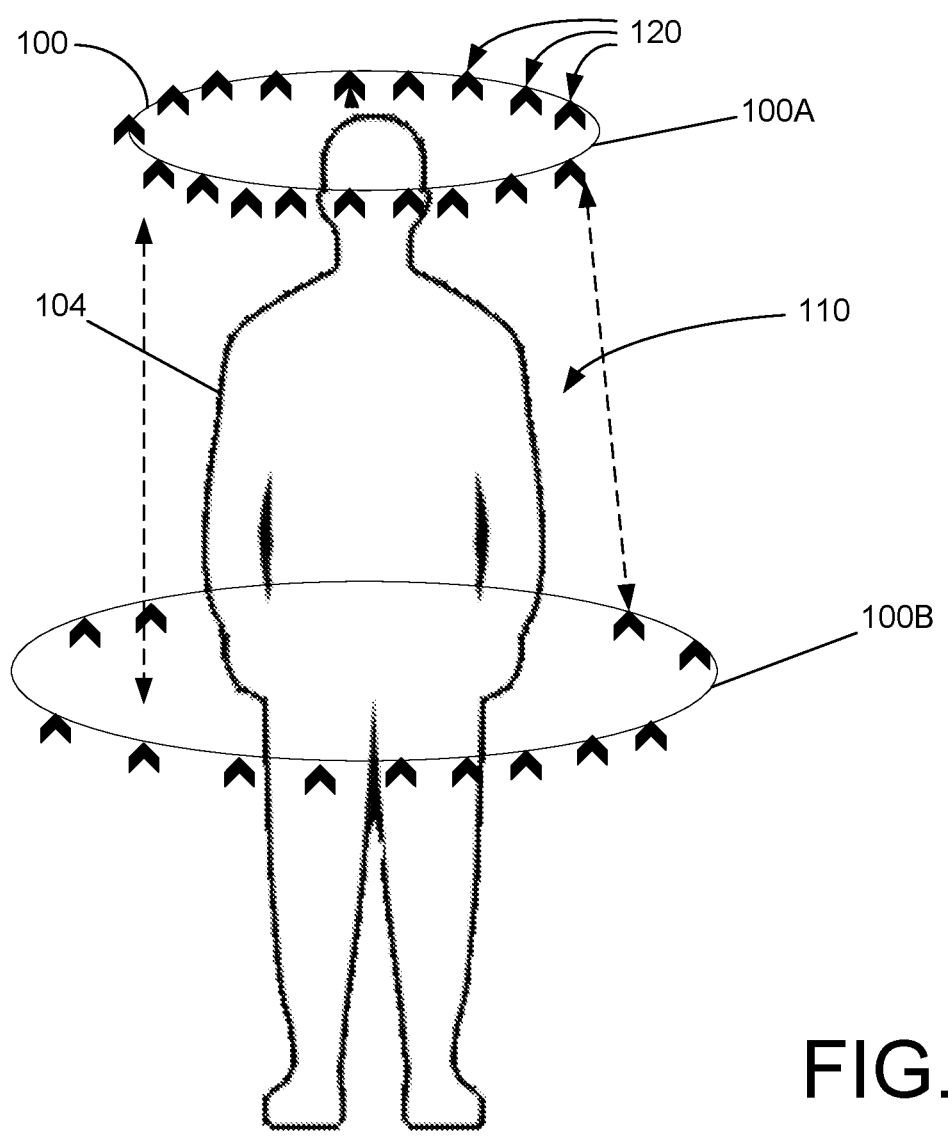
FIG. 1A is a front view of an example of a sample collection apparatus for collecting a sample for scent detection according to an embodiment.

FIG. 1A is a front view of an example of a sample collection apparatus for collecting a sample for scent detection according to an embodiment. FIG. 1B is a simplified top view of the apparatus of FIG. 1A.

An air ring 100 is disposed at a top ring position 100A above the detection subject 104 typically standing in a sample collection zone 110 such as a passenger portal at a passenger screening area or checkpoint. The air ring 100 may be a circumferential ring tubing 100 formed of one continuous tubing or a plurality of linear and/or curvilinear tubes connected together. It includes a plurality of air nozzles 120 that are distributed along a circumferential length of the air ring 100 and pointed inwardly toward an interior (e.g., center or central axis) of the sample collection zone 110 and downwardly toward the bottom of the sample collection zone 110. The range of possible nozzle angles may be between about 0° (horizontally inward) and less in magnitude than about −90° (vertically downward), or between 0° and about −60° (partially inward and partially downward), or between 0° and about −30°, or between about −5° and about −15°. The air ring 100 may be controlled to move or slide downwardly from the top ring position 110A to a lower position 110B, for instance, down to a bottom ring position at or near a bottom of the detection subject such as a platform on which the detection subject 104 stands. The air flow forms a sheet of air acting as a boundary layer that pushes particles and vapor as a sample of the detection subject 104 downward, for instance, toward a sample receptacle.

The plurality of air nozzles 120 along the circumferential length of the circumferential ring tubing 100 direct air flow toward the interior as the circumferential ring tubing 100 is moved from the top ring tubing position 100A to the bottom ring tubing position to blow air toward the detection subject 104 in the sample collection zone 110 in the interior, to push a sample of the detection subject 104 via an air flow downward toward the platform on which the detection subject 104 is positioned. The sample includes particles and/or vapor of the detection subject 104.

The nozzle angles of the air nozzles 120 may be fixed or adjustable. In one embodiment, the nozzle angle may be fixed during movement of the air ring 100 from the top ring position 100A to the bottom ring position. In another embodiment, the nozzle angle may be adjusted during movement of the air ring 100 from the top ring position 100A to the bottom ring position; this may improve sample collection. The air ring tubing 100 may have a circular cross-section and the nozzles 120 may be configured to be rotatable around the circular cross-section of the air ring tubing 100 to adjust the nozzle angle. A nozzle controller may be provided to rotate the nozzles 120 during movement of the air ring 100 from the top ring position 100A to the bottom ring position. The nozzle angle may be adjusted as a function of the vertical or translational position of the air ring 100. For instance, the nozzle angle may gradually change to an increasingly downward orientation as the air ring 100 moves closer to the bottom ring position to push the sample toward the collection receptacle more effectively.

As seen in FIGS. 1A and 1B, the air ring 100 has an oval or elliptical shape with a major diameter and a minor diameter. In another embodiment, the air ring 100 may be a circle. Still other embodiments may provide other linear and/or curvilinear shapes for the air ring 100. The ring 100 of nozzles 120 may have an adjustable lateral position (e.g., varying major and minor diameters) to keep the nozzles in close proximity of the detection subject 104 (i.e., moving inwardly to form a smaller ring around the head, moving outwardly to form a larger ring around the shoulder and the core and the hip, and moving inwardly to form a smaller ring around the lower legs).

Figure 2:
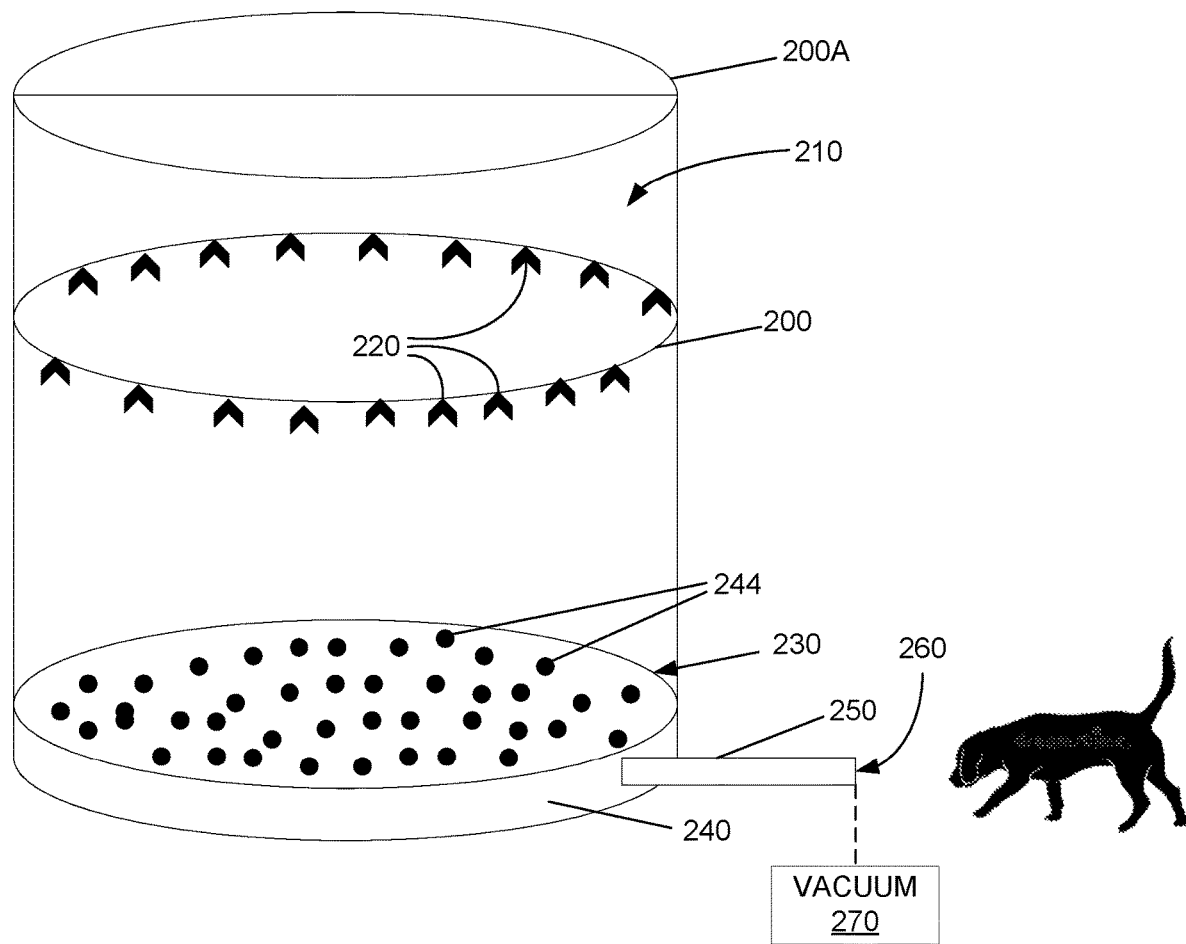
FIG. 2 is a front view of an example of an open screening portal which includes a sample collection apparatus for collecting a sample for scent detection according to another embodiment.

FIG. 2 is a front view of an example of an open screening portal which includes a sample collection apparatus for collecting a sample for scent detection according to another embodiment. An air ring 200 slides from a top ring position 200A above the detection subject typically standing in a sample collection zone 210. It includes a plurality of air nozzles 220 that are pointed inwardly toward the interior of the sample collection zone 210 and downwardly toward the bottom of the sample collection zone 210. At the bottom is a platform 230 on which the detection subject may stand or to which the detection subject is connected. The air ring 200 is controlled to move or slide downwardly from the top ring position 200A to a bottom ring position at or near the platform 230. A sample receptacle 240 may be disposed below the platform 230 which includes a plurality of collection receptors 244 such as perforations or openings through the platform 230, to collect the sample of the detection subject carried by the air flow through the plurality of collection receptors 244 of the platform 230 to the receptacle 240.

The air flow from the air ring 200 of nozzles 220 forms a sheet of air acting as a boundary layer that pushes particles and vapor of the detection subject downward toward the collection receptors 244. This action causes the air flow to drive particles and vapor of the detection subject through the collection receptors 244 to the sample receptacle 240. A vacuum or negative pressure 270 may be provided to help draw the air flow into the sample receptacle 240. A receptor tunnel or receptor channel 250 may be connected to the sample receptacle 240 to direct the air flow of particles and vapor collected at the sample receptacle 240 toward an outlet 260 where a dog is located to perform scent detection of the sample. One benefit is the dog can be separated from the detection subject and does not interact with the detection subject, unlike the approach disclosed in U.S. Pat. No. 10,123,509.

Figure 3:
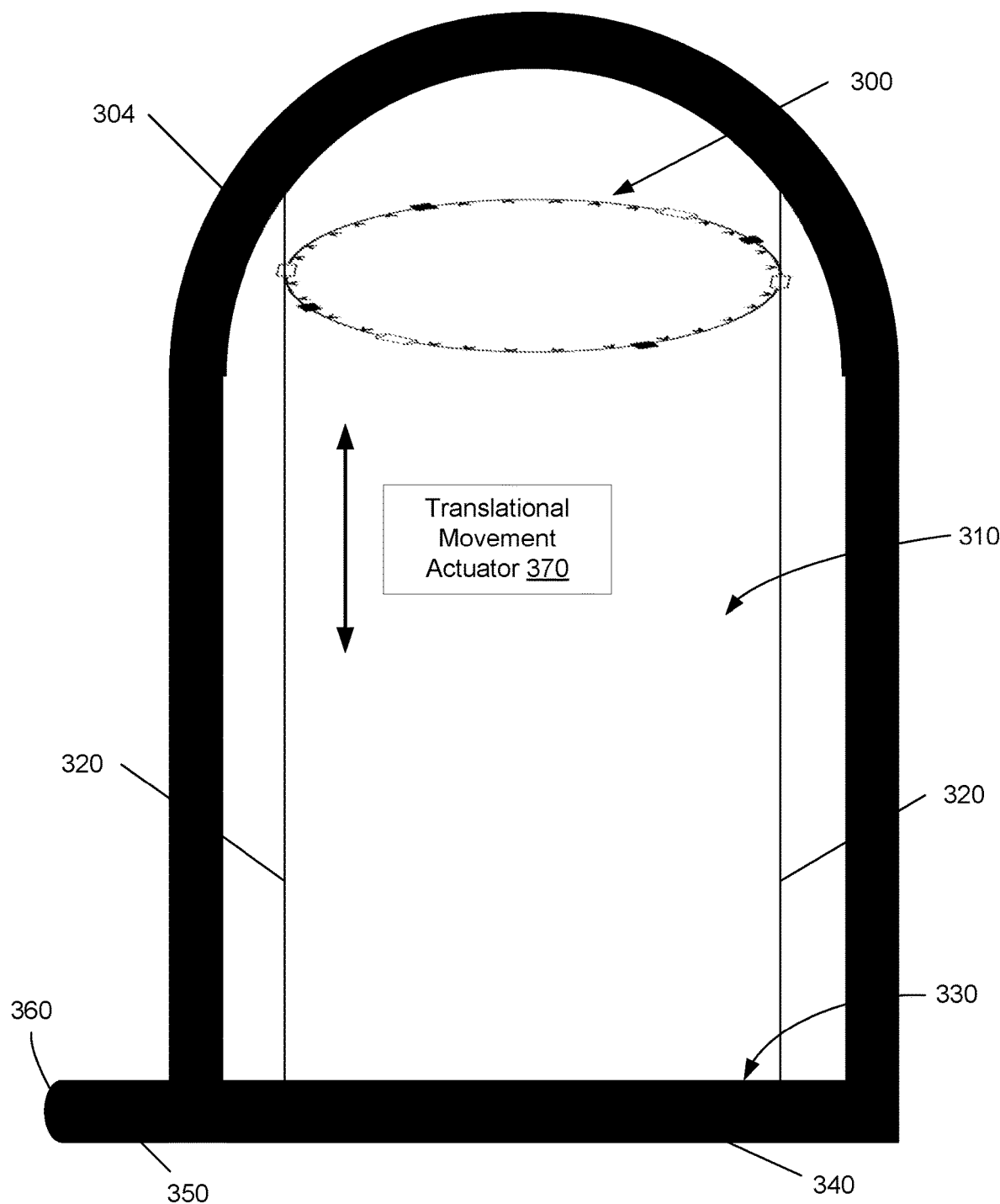
FIG. 3 is a front view of an example of an enclosed screening portal which includes a sample collection apparatus for collecting a sample for scent detection according to another embodiment.

FIG. 3 is a front view of an example of an enclosed screening portal which includes a sample collection apparatus for collecting a sample for scent detection according to another embodiment. An air ring 300 is disposed inside the enclosed screening portal or enclosure 304 which may be open or closed. An open enclosure 304 may have an enclosure opening for the detection subject to enter and exit the enclosure 304. In another example, there may be an entrance enclosure opening and an exit enclosure opening for the detection subject to walk into the enclosure, get tested, and walk through and out of the enclosure 304. The enclosure opening(s) may include door(s) that can be closed to provide a more controlled environment of a closed enclosure in which to drive the sample using the ring 300 of air nozzles and collect the sample.

The air ring 300 may be a pneumatic ring employing a plurality of sensors for detecting the shape and size of the detection subject to produce detection data, which may then be used to control adjustment of the circumferential length of the circumferential ring tubing 300. The air ring 300 may include a plurality of air blowers or nozzles for blowing air inwardly toward the interior of a sample collection zone 310 and downwardly toward the bottom of the sample collection zone 310. To guide up and down movements of the pneumatic ring 300, stanchions or lines 320 may be used. The stanchions 320 may be fixed and may be attached to the base or platform 330 and/or the top of the enclosure 304. The stanchions 320 may be rigid or flexible laterally. The pneumatic ring 300 is slidably attached to the translational stanchions 320 to travel translationally between a top ring position and a bottom ring position. In one example, the stanchions are vertical stanchions 320. The bottom ring position may be at the platform 330 or a short distance (e.g., several inches) above the platform 330.

A sample receptacle 340 may be disposed below or adjacent the platform 330 which includes a plurality of collection receptors such as perforations or openings through the platform 330. The air flow from the air ring 300 of nozzles forms a sheet of air acting as a boundary layer that pushes a sample of particles and vapor of the detection subject downward toward the collection receptors through the platform 330, driving the sample through the collection receptors to the sample receptacle 340. A vacuum or negative pressure may be provided to help draw the air flow into the sample receptacle 340. A receptor tunnel or receptor channel 350 may be connected to the sample receptacle 340 to direct the air flow of particles and vapor collected at the sample receptacle 340 through an outlet 360 to a sample analysis location where the collected sample is analyzed.

One or more translational movement actuators 370 may be used to control translational movement of the air ring 300 along the stanchions 320. In one example, the actuators are vertical movement actuators 370. In other examples, the translational movement is not vertical but any forward and backward movement, including inclined movement and even horizontal movement. Furthermore, the vertical movement actuators 370 may move the air ring 300 upward from the bottom ring tubing position to the top ring tubing position for collecting the sample, instead of downward. In general, the air ring 300 starts from a ring tubing initiation position at or near an initiation end of the detection subject (top air ring position at or above the top of the detection subject in the examples of FIGS. 2 and 3) and is driven forward (downward in the examples of FIGS. 2 and 3) by the translational movement actuators 370 to a ring tubing collection position at or near a collection end of the detection subject (bottom air ring position at or near the bottom of the detection subject in the examples of FIGS. 2 and 3) for sample collection. The "forward" direction is downward in FIGS. 2 and 3, but may be an upward direction in another embodiment and may be any other nonvertical direction in other embodiments. The translational movement actuators 370 may be disposed on the air ring 300 or the stanchions 320, or connected thereto from a remote location, and these actuators 370 may be mechanical, pneumatic, electrical, or the like. This is one example mechanism or means for guiding forward movement of the circumferential ring tubing 300 between the ring tubing initiation position and the ring tubing collection position. Other mechanisms, which may be mechanical or of some other type, can be used in other embodiments.

Figure 4:
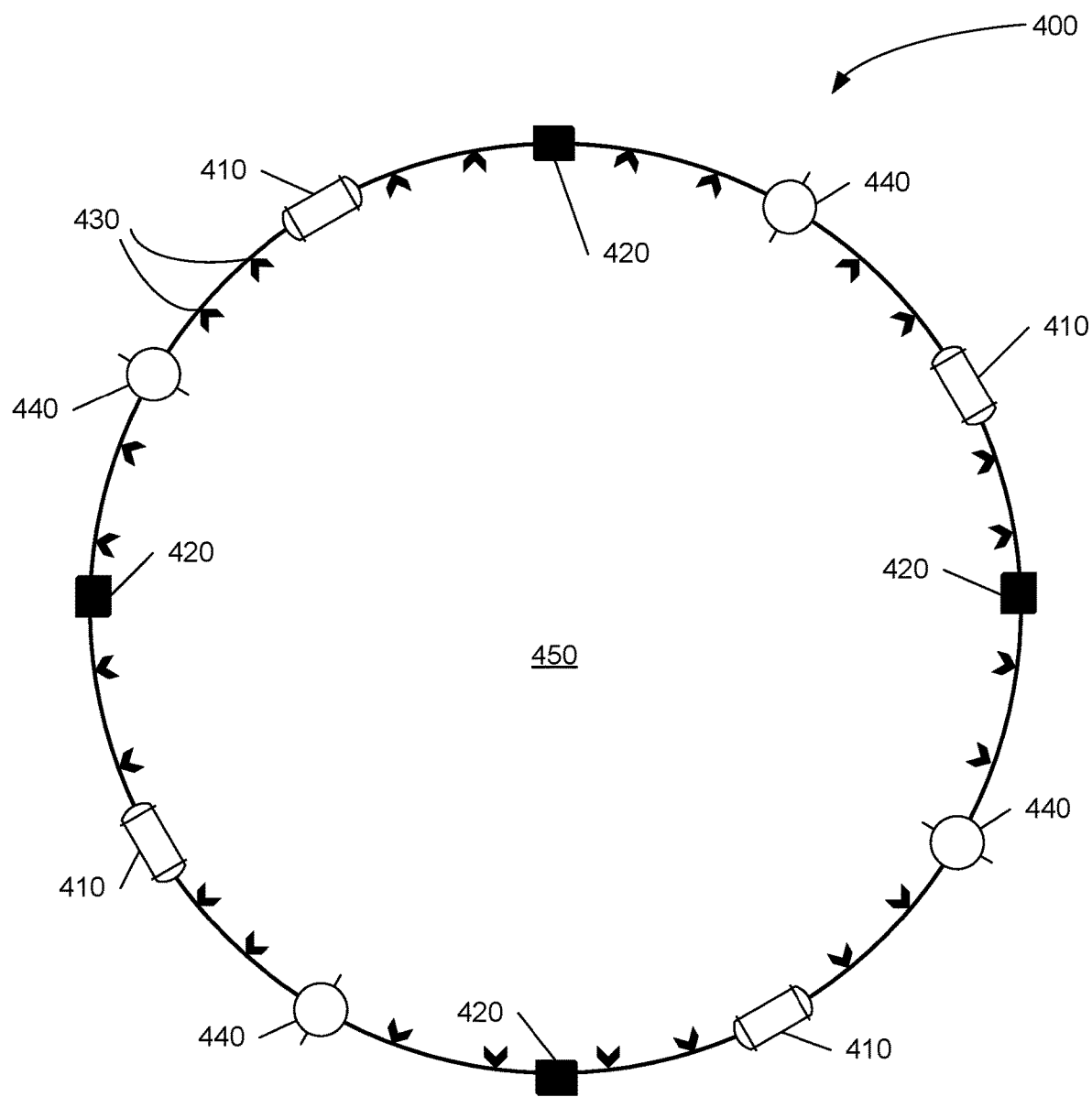
FIG. 4 is a simplified top view of an air ring in the sample collection apparatus of FIG. 3.

FIG. 4 is a simplified top view of an example of an air ring in the sample collection apparatus of FIG. 3. The air ring is a circular pneumatic air ring 400. In other embodiments, the air ring 400 may be oval or elliptical or some other linear and/or curvilinear shape.

The pneumatic air ring 400 may include a plurality of pneumatic devices 410 for driving air through the air nozzles 430 toward the sample collection zone 450 (310 in FIG. 3). The pneumatic devices 410 may be controlled locally or remotely by an operator and/or a computer. The pneumatic devices 410 may be activated only when the air ring 400 is moved from the top ring position or top ring tubing position to the bottom ring position or bottom ring tubing position.

The air ring 400 may include a plurality of circumferential length adjusting devices or actuators 440 for adjusting the size of the air ring 400. The air ring 400 shrinks or contracts in size when the circumferential length is decreased and expands in size when the circumferential length is increased. The circumferential length of the air ring tubing 400 may be changed in a telescoping manner utilizing a telescoping construction of overlapping circumferential tubes for forming the air ring tubing 400. The circumferential length adjusting devices 440 may be controlled locally or remotely by an operator and/or a computer, based on operator input and/or sensor input. This is one example mechanism or means for adjusting a circumferential length of the circumferential ring tubing to contract the circumferential ring tubing by decreasing the circumferential length and to expand the circumferential ring tubing by increasing the circumferential length. Other mechanisms, which may be mechanical or of some other type, can be used in other embodiments.

In one embodiment, the circumferential length adjusting devices 440 adjust the size of the air ring 400 based at least in part on sensors 420 that detect the shape and size of the detection subject. The sensors 420 may be disposed on the air ring 400. One example is a Lidar sensor. Lidar is an acronym for "light detection and ranging" and is sometimes called "laser scanning" or "3D scanning." The technology uses eye-safe laser beams to create a 3D representation of the surveyed environment. In this example, the Lidar sensor detects or maps the outline or outer surface (shape and size) of the body of the detection subject. This is one example mechanism or means for mapping an outer surface of the detection subject to produce mapping data. The detection information can be used to adjust the size of the air ring 400. For example, the detection information may be used to keep a consistent distance between the air ring 400 and the body while traveling from head to toe. A computerized process may be used to link the detection result of the sensors 420 via computer control to the circumferential length adjusting devices 440 to change the size of the air ring 400 to keep the distance between the air ring 400 and the body consistent (e.g., within a preset distance range of several inches or the like). This is one example mechanism or means for adjusting the circumferential length of the circumferential ring tubing, based on the mapping data, to keep a distance between the circumferential ring tubing and the outer surface of the detection subject to within a preset distance range. Other mechanisms, which may be mechanical or of some other type, can be used in other embodiments.

FIG. 4 shows four pneumatic devices 410, four sensors 420, and four circumferential length adjusting devices 440, which may be distributed evenly along the circumferential length of the air ring 400. More or fewer pneumatic devices 410, sensors 420, and circumferential length adjusting devices 440 may be used. The number of sensors 420 and the number of circumferential length adjusting devices 440 may be different from one another in some embodiments.

A plurality of air blowers or nozzles 430 are distributed along the circumferential length of the air ring 400 for blowing air inwardly toward the interior of the sample collection zone 450 and downwardly toward the bottom of the sample collection zone 450 such as the platform 330. To guide up and down movements of the pneumatic ring 400, the stanchions 320 of FIG. 3 may be provided between the base or platform 330 and the top of the enclosure 404. The stanchions 320 may be fixed at the top and/or the bottom but have sufficient lateral flexibility or compliance to accommodate the shrinking and expansion of the air ring 400 as it slides up and down the sample collection zone 450.

Figure 5:
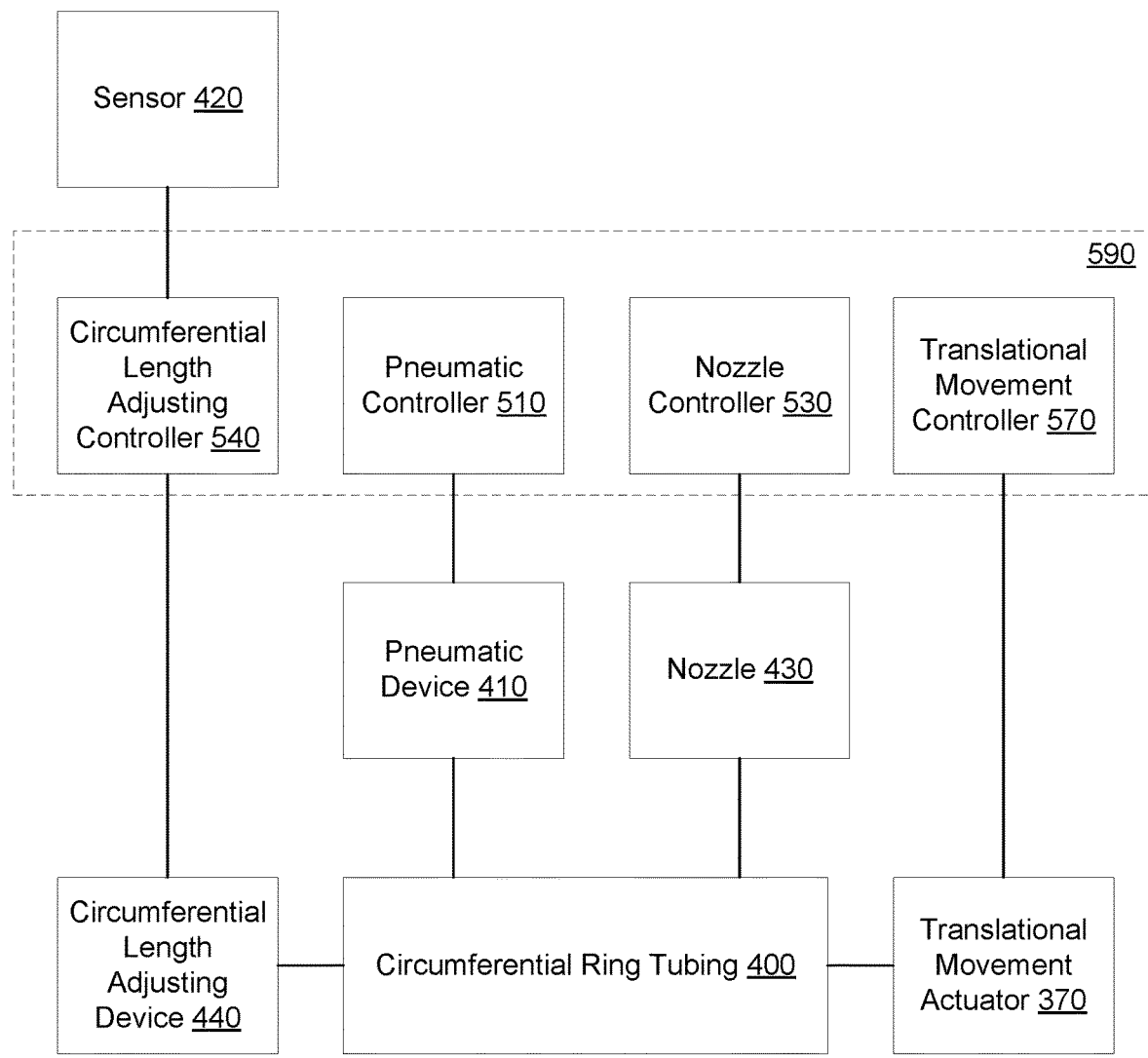
FIG. 5 is a block diagram of an example of a control system of the sample collection apparatus according to an embodiment.

FIG. 5 is a block diagram of an example of a control system of the sample collection apparatus according to an embodiment. These may include control of the translational movement of the air ring tubing 400 using the translational movement actuators 370, control of the circumferential length adjustment of the air ring tubing 400 using the circumferential length adjusting devices 440, control of the nozzle angle of the nozzles 430 by rotating the nozzles 430, and control of the air flow through the air nozzles 430 on the air ring tubing 400 using the pneumatic devices 410.

The translational movement actuators 370 may be controlled by one or more translational movement controllers 570, which may be disposed on the air ring 400 or the stanchions 320, or connected to the translational movement actuators 370 from a remote location. The controllers 570 may be separate from or integrally constructed with the translational movement actuators 370, to control translational movement of the air ring 400 along the stanchions 320. The control may involve moving the air ring 400 to an initial position at the top ring position for a current sample collection cycle, controlling the speed of descent from the top ring position, moving the air ring 400 to a final position at the bottom ring position, and returning the air ring 400 to the top ring position for the next sample collection cycle. The control may be manually set by the operator or automatically set by a computer, or a combination of both.

The circumferential length adjusting devices 440 may be controlled by one or more circumferential length adjusting controllers 540, which may be disposed on the air ring 400 or connected to the circumferential length adjusting devices 440 from a remote location. The controllers 540 may be separate from or integrally constructed with the circumferential length adjusting devices 440, to control circumferential length adjustment of the air ring 400 to change the circumferential size of the air ring 400, for example, to maintain the distance between the air ring 400 and the body of the detection subject to within a preset distance range. The controllers 540 may control the circumferential length adjusting devices 440 to change the circumferential size of the air ring 400, locally or remotely by an operator and/or a computer, based on operator input and/or sensor input of the sensors 420. The control may be manually set by the operator or automatically set by a computer, or a combination of both.

The nozzle angles of the nozzles 430 may be controlled by one or more nozzle controllers 530 to orient the nozzles 430 at specified angles toward the detection subject. The nozzle controllers 530 may be disposed on the air ring 400 or connected to the nozzles 430 from a remote location, to control the nozzle angles locally or remotely by an operator and/or a computer, based on operator input and/or vertical or translational position of the air ring 400 (e.g., in coordination with the translational movement controllers 570).

The pneumatic devices 410 may be controlled by one or more pneumatic controllers 510 for blowing air through the air nozzles 430 toward the sample collection zone 450. The pneumatic controllers 510 may be disposed on the air ring 400 or connected to the pneumatic devices 410 from a remote location. The controllers 510 may be separate from or integrally constructed with the pneumatic devices 410, to control the air flow through the air nozzles 430, locally or remotely by an operator and/or a computer. The pneumatic devices 410 may be activated only when the air ring 400 is moved from the top ring position or top ring tubing position to the bottom ring position or bottom ring tubing position.

The pneumatic controllers 510, circumferential length adjusting controllers 540, nozzle angle controllers 530, and translational movement controllers 570 can operate independently or they may be under a single master controller 590 to coordinate the controls. The master controller 590 may include a computer processor programmed to provide computer control with or without operator input via a user interface and with or without sensor input from position sensors, pneumatic sensors, mapping sensors, and the like.

Figure 6:
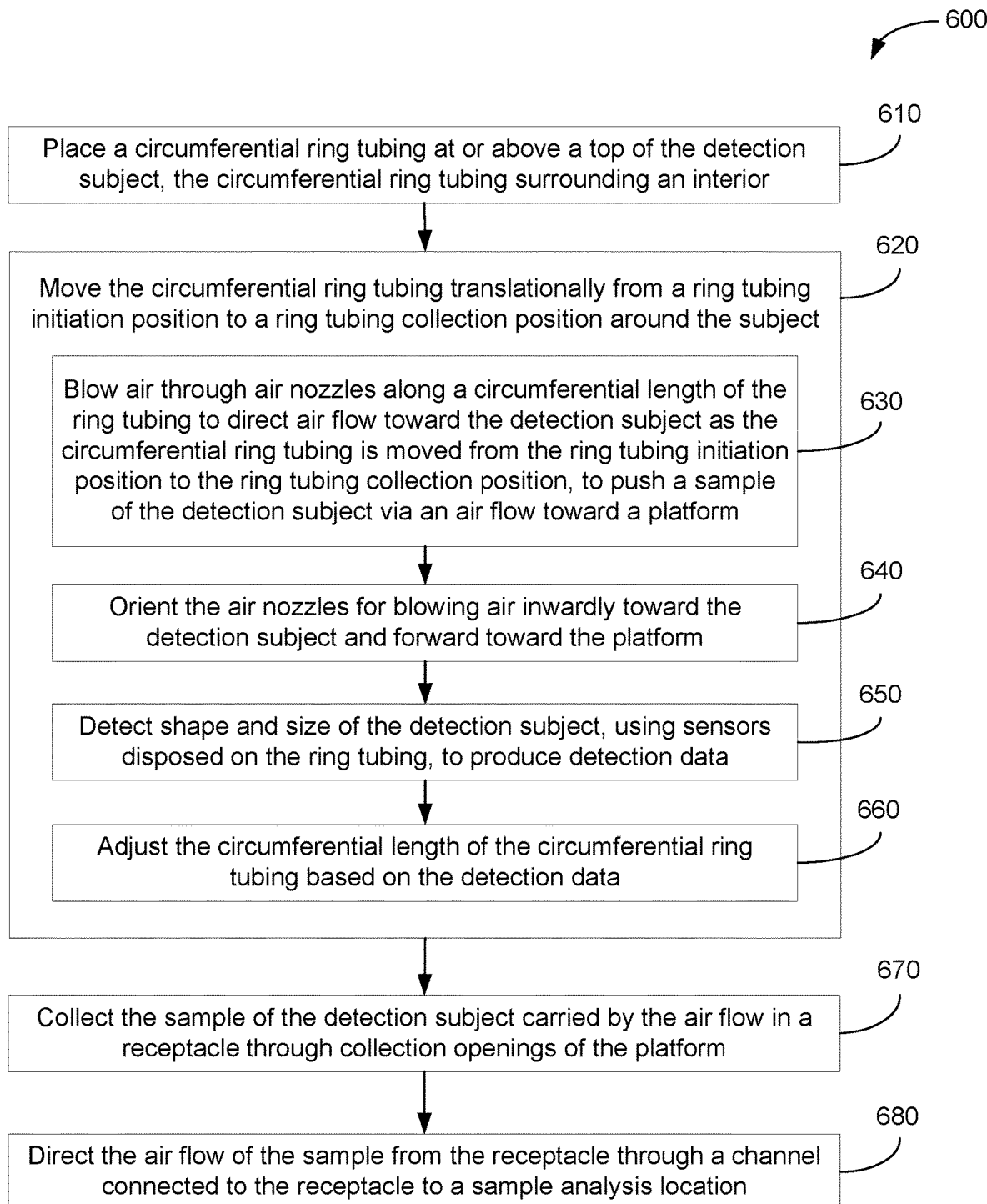
FIG. 6 is a flow diagram illustrating an example of a sample collection process.

FIG. 6 is a flow diagram illustrating an example of a sample collection process 600. Step 610 involves placing a circumferential ring tubing 400 at or near an initiation end of the detection subject (e.g., at or above a top of the detection subject), the circumferential ring tubing surrounding a sample collection zone in an interior. Step 620 involves moving the circumferential ring tubing 400 translationally from a ring tubing initiation position to a ring tubing collection position (e.g., vertically from a top ring tubing position to a bottom ring tubing position in the examples of FIGS. 2 and 3) around the detection subject in the sample collection zone.

Steps 630 to 660 may be performed during step 620 of moving the circumferential ring tubing 400 from top to bottom. In step 630, air is blown through air nozzles 430 along a circumferential length of the circumferential ring tubing 400 to direct air flow toward the detection subject as the circumferential ring tubing 400 is moved from the ring tubing initiation position to the ring tubing collection position, to push a sample of the detection subject via an air flow forward toward a platform 330. In step 640, the air nozzles are oriented for blowing air inwardly toward the detection subject and forward toward the platform 330. Step 650 involves detecting the shape and size of the detection subject, using sensors 420 disposed on the ring tubing 400, to produce detection data. In step 660, the circumferential length of the circumferential ring tubing 400 is adjusted based on the detection data to change the size of the circumferential ring tubing 400, for example, to maintain the distance between the ring tubing 400 and the body of the detection subject to within a preset distance range.

Step 670 involves collecting the sample of the detection subject carried by the air flow in a receptacle 340 disposed beyond or adjacent the platform 330 through collection openings. In step 680, the air flow of the sample is directed from the receptacle 340 through a channel 350 connected to the receptacle through an outlet 360 to a sample analysis location.

The sample collection apparatus benefits screening because it collects particles as well as vapor. The design is based on large molecular weights of explosives with respect to air (e.g., up to an order of magnitude larger or more) and the deficit of available sample. Features such as the number of nozzles, air flow rates, and design of the collection receptors and sample receptacle at the bottom may be determined or selected for optimization. Additional features include compressed air connections, doors, and slides. The sample collection zone or passenger portal may be open, partially enclosed, or completely enclosed.

The detection subject is a stationary target. The directed air flow drives the vapor and/or particles of the subject from the stationary target to an outlet where the canine is positioned which is generally a stationary position. It is relatively easy to achieve appropriate positioning of the canine in the stationary system to maximize the air flow and scents that the canine is able to analyze. The canine does not need to move around in an open space to follow the subject being detected and choke points and crowds are of no concern.

Unlike the nonstationary or mobile environment in which fans are used to generate air currents which assist the canine in detecting explosive odor, the stationary environment (especially if the subject is enclosed) provides better and more reliable control of the air flow by eliminating variables of fan placement, crowd interference, other crowd or mobile effects, and the like. It also eliminates the need for special training of canine to perform vapor wake screening such as that described in U.S. Pat. No. 10,213,509.

In one example, the ring of nozzles maintains a constant lateral position (e.g., constant diameter of a circle) as it moves from the top ring position to the bottom ring position. In another embodiment, the ring of nozzles has an adjustable lateral position (e.g., varying diameter) to keep the nozzles in close proximity within a preset distance range of the detection subject (i.e., moving inwardly to form a smaller ring around the head, moving outwardly to form a larger ring around the shoulder and the core and the hip, and moving inwardly to form a smaller ring around the legs).

In one embodiment, the detection is performed by a dog which is used as a sniffing or scent detection mechanism. In another embodiment, the detection is performed by another kind of animal with a superior sense of smell such as rodents and other mammals for scent detection.

Figure 7:
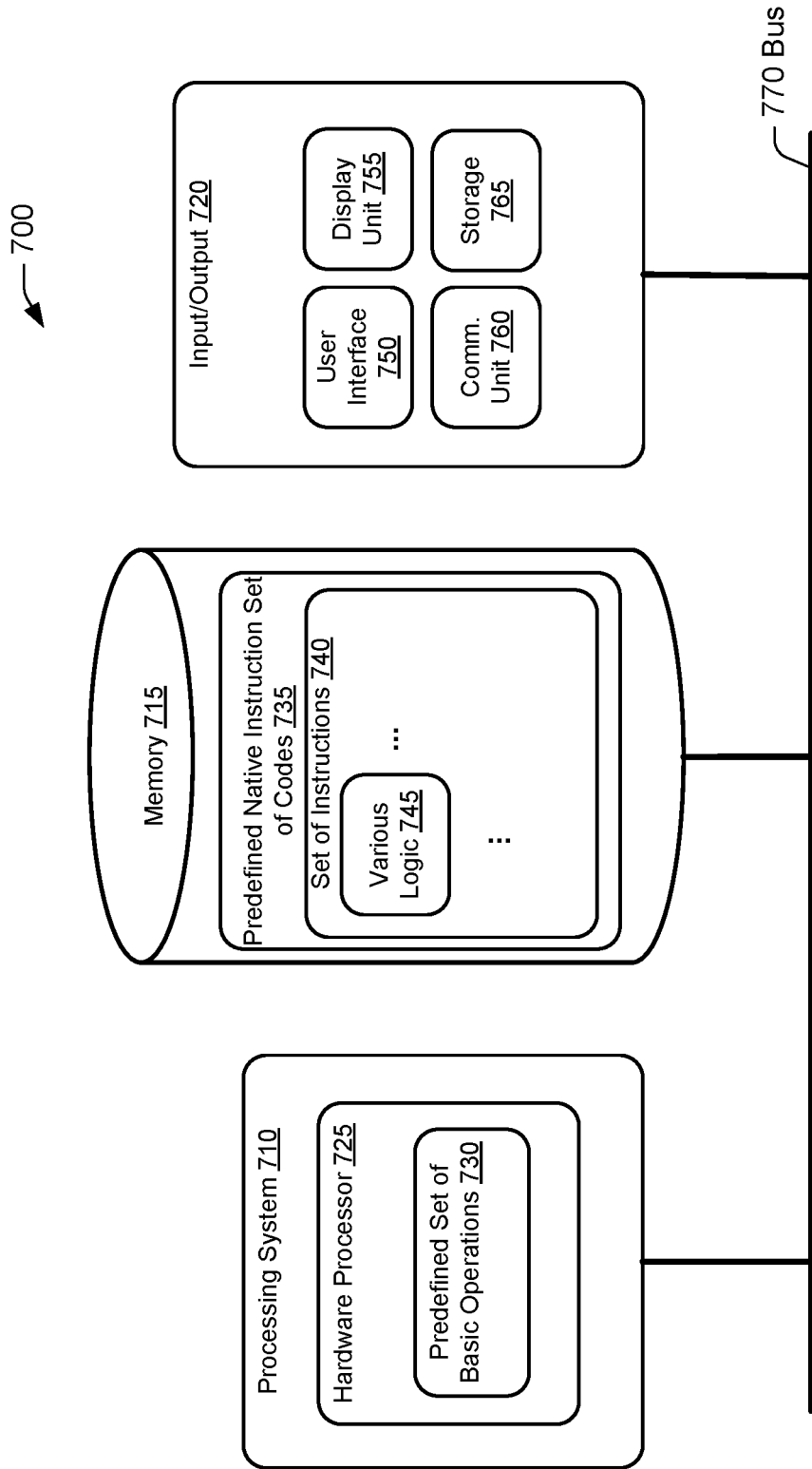
FIG. 7 illustrates a computing system including logic according to an embodiment.

FIG. 7 illustrates a computing system 700 including logic according to an embodiment. The computing system 700 includes a processing system 710 having a hardware processor 725 configured to perform a predefined set of basic operations 730 by loading corresponding ones of a predefined native instruction set of codes 735 as stored in the memory 715. The computing system 700 further includes input/output 720 having user interface 750, display unit 755, communication unit 760, and storage 765. The computing system 700 can be used to implement some or all of the processes or operations of the controllers (510, 530, 540, and 570) in FIG. 5.

The memory 715 is accessible to the processing system 710 via the bus 770. The memory 715 includes the predefined native instruction set of codes 735, which constitute a set of instructions 740 selectable for execution by the hardware processor 725. In an embodiment, the set of instructions 740 include logic 745 representing various processor logic and/or modules. An example of such logic 745 is set forth in greater detail with respect to the flow diagram illustrated in FIG. 1. Each of the above-mentioned algorithms (e.g., MMWI, neutron imaging, and other detection algorithms and other imaging algorithms) can be a separate system or a module in an overall computer system 700. The various logic 745 is stored in the memory 715 and comprises instructions 740 selected from the predefined native instruction set of codes 735 of the hardware processor 725, adapted to operate with the processing system 710 to implement the process or processes of the corresponding logic 745.

A hardware processor may be thought of as a complex electrical circuit that is configured to perform a predefined set of basic operations in response to receiving a corresponding basic instruction selected from a predefined native instruction set of codes. The predefined native instruction set of codes is specific to the hardware processor; the design of the processor defines the collection of basic instructions to which the processor will respond, and this collection forms the predefined native instruction set of codes. A basic instruction may be represented numerically as a series of binary values, in which case it may be referred to as a machine code. The series of binary values may be represented electrically, as inputs to the hardware processor, via electrical connections, using voltages that represent either a binary zero or a binary one. These voltages are interpreted as such by the hardware processor. Executable program code may therefore be understood to be a set of machine codes selected from the predefined native instruction set of codes. A given set of machine codes may be understood, generally, to constitute a module. A set of one or more modules may be understood to constitute an application program or "app." An app may interact with the hardware processor directly or indirectly via an operating system. An app may be part of an operating system.

A computer program product is an article of manufacture that has a computer-readable medium with executable program code that is adapted to enable a processing system to perform various operations and actions. Non-transitory computer-readable media may be understood as a storage for the executable program code. Whereas a transitory computer-readable medium holds executable program code on the move, a non-transitory computer-readable medium is meant to hold executable program code at rest. Non-transitory computer-readable media may hold the software in its entirety, and for longer duration, compared to transitory computer-readable media that holds only a portion of the software and for a relatively short time. The term, "non-transitory computer-readable medium," specifically excludes communication signals such as radio frequency signals in transit. The following forms of storage exemplify non-transitory computer-readable media: removable storage such as a USB disk, a USB stick, a flash disk, a flash drive, a thumb drive, an external SSD, a compact flash card, an SD card, a diskette, a tape, a compact disc, an optical disc; secondary storage such as an internal hard drive, an internal SSD, internal flash memory, internal non-volatile memory, internal DRAM, ROM, RAM, and the like; and the primary storage of a computer system.

Different terms may be used to express the relationship between executable program code and non-transitory computer-readable media. Executable program code may be written on a disc, embodied in an application-specific integrated circuit, stored in a memory chip, or loaded in a cache memory, for example. Herein, the executable program code may be said, generally, to be "in" or "on" a computer-readable media. Conversely, the computer-readable media may be said to store, to include, to hold, or to have the executable program code.

The inventive concepts taught by way of the examples discussed above are amenable to modification, rearrangement, and embodiment in several ways. For example, this invention may be applicable for collecting samples from inanimate objects as well as live detection subjects. Moreover, the sample analysis may involve types of analysis other than scent detection using animals. For example, a piece of illicit material detection equipment such as an explosive trace detector (ETD) may be used to analyze the collected sample in the sample analysis area or location. Accordingly, although the present disclosure has been described with reference to specific embodiments and examples, persons skilled in the art will recognize that changes may be made in form and detail without departing from the spirit and scope of the disclosure.

Certain attributes, functions, steps of methods, or sub-steps of methods described herein may be associated with physical structures or components, such as a module of a physical device that, in implementations in accordance with this disclosure, make use of instructions (e.g., computer executable instructions) that are embodied in hardware, such as an application specific integrated circuit, or that may cause a computer (e.g., a general-purpose computer) executing the instructions to have defined characteristics. There may be a combination of hardware and software such as processor implementing firmware, software, and so forth so as to function as a special purpose computer with the ascribed characteristics. For example, in embodiments a module may comprise a functional hardware unit (such as a self-contained hardware or software or a combination thereof) designed to interface the other components of a system such as through use of an API. In embodiments, a module is structured to perform a function or set of functions, such as in accordance with a described algorithm. This disclosure may use nomenclature that associates a component or module with a function, purpose, step, or sub-step to identify the corresponding structure which, in instances, includes hardware and/or software that function for a specific purpose. For any computer-implemented embodiment, "means plus function" elements will use the term "means;" the terms "logic" and "module" and the like have the meaning ascribed to them above, if any, and are not to be construed as means.

The claims define the invention and form part of the specification. Limitations from the written description are not to be read into the claims.

An interpretation under 35 U.S.C. § 112(f) is desired only where this description and/or the claims use specific terminology historically recognized to invoke the benefit of interpretation, such as "means," and the structure corresponding to a recited function, to include the equivalents thereof, as permitted to the fullest extent of the law and this written description, may include the disclosure, the accompanying claims, and the drawings, as they would be understood by one of skill in the art.

To the extent the subject matter has been described in language specific to structural features and/or methodological steps, it is to be understood that the subject matter defined in the appended claims is not necessarily limited to the specific features or steps described. Rather, the specific features and steps are disclosed as example forms of implementing the claimed subject matter. To the extent headings are used, they are provided for the convenience of the reader and are not be taken as limiting or restricting the systems, techniques, approaches, methods, devices to those appearing in any section. Rather, the teachings and disclosures herein can be combined, rearranged, with other portions of this disclosure and the knowledge of one of ordinary skill in the art. It is the intention of this disclosure to encompass and include such variation. The indication of any elements or steps as "optional" does not indicate that all other or any other elements or steps are mandatory.

What is claimed is:

1. A sample collection apparatus to collect sample from a detection subject comprising:
    a platform to support a detection subject on which a bottom of the detection subject is positioned;
    a circumferential ring tubing surrounding an interior and configured to be moved generally vertically between a bottom ring tubing position and a top ring tubing position, the circumferential ring tubing including a plurality of air nozzles along a circumferential length of the circumferential ring tubing to direct air flow toward the interior as the circumferential ring tubing is moved from the top ring tubing position to the bottom ring tubing position, to blow air toward the detection subject in a sample collection zone in the interior of the circumferential ring tubing as the circumferential ring tubing is moved from the top ring tubing position to the bottom ring tubing position, and to push a sample of the detection subject via an air flow forward toward the platform below the detection subject on which the bottom of the detection subject is positioned, the sample including at least one of particles and vapor of the detection subject;
    a receptacle disposed below the platform to collect the sample of the detection subject carried by the air flow through a plurality of collection openings of the platform to the receptacle; and,
    a plurality of circumferential length adjusting telescoping actuators disposed on the circumferential ring tubing to adjust a circumferential length of the circumferential ring tubing to contract the circumferential ring tubing by decreasing the circumferential length and to expand the circumferential ring tubing by increasing the circumferential length.

2. The sample collection apparatus of claim 1,
    wherein the air nozzles are oriented between an angle of about 0° horizontally inward toward the interior of the circumferential ring tubing and an angle of less in magnitude than about −90° vertically downward.

3. The sample collection apparatus of claim 2,
    wherein the air nozzles are oriented between an angle of about −5° inward toward the interior of the circumferential ring tubing and an angle of about −15° partially inward and partially downward.

4. The sample collection apparatus of claim 1,
    wherein the circumferential ring tubing includes a plurality of linear tubes connected together; and,
    wherein the plurality of circumferential length adjusting telescoping actuators are coupled with the plurality of linear tubes of the circumferential ring tubing to adjust a circumferential length of the circumferential ring tubing to contract the circumferential ring tubing by decreasing the circumferential length and to expand the circumferential ring tubing by increasing the circumferential length.

5. The sample collection apparatus of claim 1, further comprising:
a plurality of sensors disposed on the circumferential ring tubing to detect shape and size of the detection subject to produce detection data; and
a controller to control the circumferential length adjusting telescoping actuators to adjust the circumferential length of the circumferential ring tubing based on the detection data.

6. The sample collection apparatus of claim 5,
wherein the controller is configured to control the circumferential length adjusting telescoping actuators to adjust the circumferential length of the circumferential ring tubing to keep a distance between the circumferential ring tubing and the detection subject to within a preset distance range.

7. The sample collection apparatus of claim 1, further comprising:
a plurality of translational stanchions to which the circumferential ring tubing is slidably attached to travel translationally between the top ring tubing position and the bottom ring tubing position.

8. A sample collection method to collect sample from a detection subject, the method comprising:
placing a circumferential ring tubing at a ring tubing initiation position at or near an initiation end of the detection subject, the circumferential ring tubing surrounding an interior;
moving the circumferential ring tubing translationally from the ring tubing initiation position to a ring tubing collection position at or near a platform to which the detection subject is connected,
blowing air through a plurality of air nozzles along a circumferential length of the circumferential ring tubing to direct air flow toward the interior as the circumferential ring tubing is moved from the ring tubing initiation position to the ring tubing collection position to blow air toward the detection subject in a sample collection zone in the interior of the circumferential ring tubing as the circumferential ring tubing is moved from the ring tubing initiation position to the ring tubing collection position, and to push a sample of the detection subject via an air flow forward toward the platform to which the detection subject is connected, the sample including at least one of particles and vapor of the detection subject; and
collecting the sample of the detection subject carried by the air flow through a plurality of collection openings of the platform to an opposite side of the platform from the detection subject to a receptacle; and,
adjusting a circumferential length of the circumferential ring tubing, using a plurality of circumferential length adjusting telescoping actuators disposed on the circumferential ring tubing, to contract the circumferential ring tubing by decreasing the circumferential length and to expand the circumferential ring tubing by increasing the circumferential length.

9. The sample collection method of claim 8, further comprising:
orienting the air nozzles for blowing air toward the detection subject between an angle of about 0° horizontally inward toward the interior of the circumferential ring tubing and an angle of less in magnitude than about −90° vertically downward.

10. The sample collection method of claim 9,
wherein the air nozzles are oriented between an angle of about −5° inward toward the interior of the circumferential ring tubing and an angle of about −15° partially inward and partially downward.

11. The sample collection method of claim 8,
wherein the circumferential ring tubing includes a plurality of linear tubes connected together; and
wherein the plurality of circumferential length adjusting telescoping actuators are coupled with the plurality of linear tubes of the circumferential ring tubing to adjust a circumferential length of the circumferential ring tubing to contract the circumferential ring tubing by decreasing the circumferential length and to expand the circumferential ring tubing by increasing the circumferential length.

12. The sample collection method of claim 8, further comprising:
detecting shape and size of the detection subject, using a plurality of sensors disposed on the circumferential ring tubing, to produce detection data; and
controlling the circumferential length adjusting telescoping actuators to adjust the circumferential length of the circumferential ring tubing based on the detection data.

13. The sample collection method of claim 12,
wherein the circumferential length adjusting telescoping actuators are controlled to adjust the circumferential length of the circumferential ring tubing to keep a distance between the circumferential ring tubing and the detection subject to within a preset distance range based on the detection data.

14. The sample collection method of claim 8, further comprising:
adjusting the circumferential length of the circumferential ring tubing, by controlling the circumferential length adjusting telescoping actuators, to keep a distance between the circumferential ring tubing and the detection subject to within a preset distance range.

15. The sample collection method of claim 8, further comprising:
slidably attaching the circumferential ring tubing to a plurality of translational stanchions to travel translationally between the ring tubing initiation position and the ring tubing collection position; and
moving the circumferential ring tubing translationally from the ring tubing initiation position to a ring tubing collection position at or near the platform to which the detection subject is connected.

16. A sample collection apparatus to collect sample from a detection subject comprising:
a platform to support a detection subject, the platform having a plurality of collection openings;
a sample receptacle; and
a circumferential ring tubing surrounding an interior and configured to be moved between an ring tubing initiation position and a ring tubing collection position, the circumferential ring tubing including a plurality of air nozzles along a circumferential length of the circumferential ring tubing to direct air flow toward the interior as the circumferential ring tubing is moved from the ring tubing initiation position forward to the ring tubing collection position, to blow air toward the detection subject in a sample collection zone in the interior of the circumferential ring tubing as the circumferential ring tubing is moved from the ring tubing initiation position to the ring tubing collection position, and to push a sample of the detection subject via an air flow forward through the plurality of collection openings of the platform to an opposite side of the platform from the detection subject toward the sample receptacle, the sample including at least one of particles and vapor of the detection subject; and, a plurality of circumferential length adjusting telescoping actuators to adjust a circumferential length of the circumferential ring tubing to contract the circumferential ring tubing by decreasing the circumferential length and to expand the circumferential ring tubing by increasing the circumferential length.

17. The sample collection apparatus of claim 16, wherein the air nozzles are oriented between an angle of about 0° horizontally inward toward the interior of the circumferential ring tubing and an angle of about −30° partially inward and partially forward.

18. The sample collection apparatus of claim 16, wherein the circumferential ring tubing includes a plurality of linear tubes connected together; and, wherein the plurality of circumferential length adjusting telescoping actuators are coupled with the plurality of linear tubes of the circumferential ring tubing to adjust a circumferential length of the circumferential ring tubing to contract the circumferential ring tubing by decreasing the circumferential length and to expand the circumferential ring tubing by increasing the circumferential length.

19. The sample collection apparatus of claim 16, further comprising:

means for mapping an outer surface of the detection subject to produce mapping data; and a controller to control the circumferential length adjusting telescoping actuators to adjust the circumferential length of the circumferential ring tubing, based on the mapping data, to keep a distance between the circumferential ring tubing and the outer surface of the detection subject to within a preset distance range.

20. The sample collection apparatus of claim 16, further comprising:

means for guiding forward movement of the circumferential ring tubing between the ring tubing initiation position and the ring tubing collection position.

* * * * *